(12) United States Patent
You et al.

(10) Patent No.: US 11,460,684 B2
(45) Date of Patent: *Oct. 4, 2022

(54) METHOD OF OPERATING A SURGICAL MICROSCOPE AND SURGICAL MICROSCOPE

(71) Applicant: Carl Zeiss Meditec AG, Jena (DE)

(72) Inventors: Fang You, Aalen (DE); David Dobbelstein, Ulm (DE); Stefan Saur, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/322,784

(22) Filed: May 17, 2021

(65) Prior Publication Data
US 2021/0271065 A1 Sep. 2, 2021

Related U.S. Application Data

(63) Continuation of application No. 16/732,126, filed on Dec. 31, 2019, now Pat. No. 11,048,072.

(51) Int. Cl.
*G02B 21/36* (2006.01)
*A61B 90/25* (2016.01)
(Continued)

(52) U.S. Cl.
CPC ............ *G02B 21/362* (2013.01); *A61B 90/25* (2016.02); *G02B 21/0012* (2013.01);
(Continued)

(58) Field of Classification Search
CPC .............. G02B 21/362; G02B 21/0012; G02B 21/365; G02B 21/368; A61B 90/25;
(Continued)

(56) References Cited

U.S. PATENT DOCUMENTS 5,825,982 A 10/1998 Wright et al.
7,190,513 B2 * 3/2007 Obrebski ........... G02B 21/0004
359/384

(Continued)

FOREIGN PATENT DOCUMENTS

WO 2015151447 A1 10/2015
WO 2018078470 A1 5/2018

OTHER PUBLICATIONS

U.S. Appl. No. 16/732,162, filed Dec. 31, 2019, Fang You et al., Carl Zeiss Meditec AG.

(Continued)

*Primary Examiner* — Hesham K Abouzahra
(74) *Attorney, Agent, or Firm* — Falk Ewers; Ewers IP Law PLLC

(57) ABSTRACT

A method of operating a surgical microscope includes detecting an amount of movement of a body portion of a user, and performing movements of a camera and changes in a magnification based on the detected movements of the body portion. The amounts of these movements and changes decrease with increasing magnification provided by the surgical microscope, they decrease with decreasing distance of the body portion of the user from the display, and they decrease with decreasing distance of the cameras from the field of view of the cameras.

74 Claims, 3 Drawing Sheets

(51) Int. Cl.
  *G06T 7/285* (2017.01)
  *H04N 13/332* (2018.01)
  *H04N 13/296* (2018.01)
  *H04N 13/239* (2018.01)
  *H04N 5/232* (2006.01)
  *G02B 21/00* (2006.01)
  *H04N 5/225* (2006.01)

(52) U.S. Cl.
  CPC ......... *G02B 21/365* (2013.01); *G02B 21/368* (2013.01); *G06T 7/285* (2017.01); *H04N 5/2253* (2013.01); *H04N 5/23216* (2013.01); *H04N 5/23296* (2013.01); *H04N 5/23299* (2018.08); *H04N 13/239* (2018.05); *H04N 13/296* (2018.05); *H04N 13/332* (2018.05); *G06T 2207/10012* (2013.01); *G06T 2207/10056* (2013.01); *G06T 2207/30004* (2013.01); *G06T 2207/30196* (2013.01); *G06T 2207/30244* (2013.01); *H04N 5/23203* (2013.01)

(58) Field of Classification Search
  CPC .... G06T 7/285; H04N 13/332; H04N 13/296; H04N 13/239; H04N 5/23299; H04N 5/2253; H04N 5/23216; H04N 5/23296
  See application file for complete search history.

(56) References Cited

U.S. PATENT DOCUMENTS

| | | | |
|---|---|---|---|
| 2017/0068081 A1* | 3/2017 | Hirayama | A61B 1/00149 |
| 2019/0008595 A1* | 1/2019 | Popovic | A61B 34/25 |
| 2019/0294103 A1* | 9/2019 | Hauger | G03H 1/0443 |

OTHER PUBLICATIONS

U.S. Appl. No. 16/732,218, filed Dec. 31, 2019, Fang You et al., Carl Zeiss Meditec AG.

\* cited by examiner

METHOD OF OPERATING A SURGICAL MICROSCOPE AND SURGICAL MICROSCOPE

CROSS REFERENCE TO RELATED APPLICATIONS

This application is a continuation of U.S. patent application Ser. No. 16/732,126 filed on Dec. 31, 2019 which relates to U.S. patent application Ser. Nos. 16/732,162, 16/732,195, and 16/732,218, filed on Dec. 31, 2019, the entire contents of which are incorporated herein by reference.

TECHNICAL FIELD

The present disclosure relates to surgical microscopes and methods of operating such surgical microscopes.

BACKGROUND

A conventional surgical microscope includes a microscope body including microscopy optics having two oculars. The microscope body is carried by a support having an articulating structure such that the microscopy optics can be positioned and repositioned relative to an object by translatory and rotatory movements. These movements are initiated by the user looking into the oculars by applying a force to the microscope body using his hands, for example. Such surgical microscopes require the user to permanently look into the oculars which is fatiguing and may create pain, for example, in the neck of the user. Moreover, the user requiring his hands for repositioning the microscope must lay aside the currently used surgical tool to the effect that the flow of the surgery is interrupted.

Newer surgical microscopes include a camera for recording images of the object under surgery, and a display for displaying the recorded images to the user of the microscope. The user can perform the surgery assuming a convenient position of the head and watch the images on the display since looking into oculars is no longer required. Moreover, the support of these microscopes may include actuators for positioning the articulated joints of the support such that the camera is positioned with a desired orientation at a desired location in space. The desired location and orientation can be inputted into the surgical microscope by various means. For example, WO 2015/151447 A1 describes a surgical microscope in which the direction of gaze of the user and movements of the head of the user are detected to determine new positions of the camera. The actuators of the support are then operated to reposition the camera according to the detected direction of gaze and head movements.

The technologies described above offer significant advantages over the conventional surgical microscope having oculars. Still, it has been found that the process of positioning the camera could be improved.

SUMMARY

The present disclosure has been achieved by taking the above considerations into account, and it is an object of the present disclosure to provide a surgical microscope and a method of operating such surgical microscope thereby improving the user experience in operations involving a repositioning of the camera.

According to an aspect of the present disclosure, a surgical microscope includes at least one camera having a field of view, a support for the at least one camera, wherein the support includes at least one actuator for positioning the at least one camera relative to an object, and a display configured to display images recorded by the at least one camera.

According to another aspect of the disclosure, a method of operating the surgical microscope includes detecting an amount of a movement of a body portion of a user, determining an amount of movement of the camera based on the detected movement of the body portion of the user, and moving the camera by the determined amount of movement.

According to an aspect of the disclosure, the determined amount of movement of the camera includes an amount of translatory movement in a direction transverse to a line connecting the camera and the field of view. The amount of translatory movement of the camera is determined in dependence of the detected amount of movement of the body portion of the user in a direction parallel to the display. The dependency between the determined amount of translatory movement of the camera and the detected amount of movement of the body portion of the user in the direction parallel to the display depends on a magnification of an image of an object within the field of view of the camera displayed on the display, a distance of the body portion of the user from the display, a distance of the camera from the field of view of the camera, and the detected amount of movement of the body portion of the user in the direction parallel to the display.

According to an exemplary embodiment, the dependency between the determined amount of translatory movement of the camera and the detected amount of movement of the body portion of the user in the direction parallel to the display is configured such that the determined amount of the translatory movement of the camera decreases when the magnification of the image of the object within the field of view of the camera displayed on the display increases.

According to a further aspect of the disclosure, the dependency between the determined amount of the translatory movement of the camera and the detected amount of movement of the body portion of the user in the direction parallel to the display is configured such that the determined amount of the translator movement of the camera decreases when the distance of the body portion of the user from the display decreases.

According to another aspect of the disclosure, the dependency between the determined amount of translatory movement of the camera and the detected amount of movement of the body portion of the user in the direction parallel to the display is configured such that the determined amount of the translatory movement of the camera decreases when the distance of the camera from the field of view of the camera decreases.

According to an aspect of the disclosure, the determining of the amount of movement of the camera is performed such that:

(1) the determined amount of translatory movement of the camera is a first determined amount when
a magnification of an image of an object within the field of view of the camera displayed on the display is a first magnification,
a distance of the body portion of the user from the display is a first body portion distance,
a distance of the camera from the field of view of the camera is a first camera distance, and
the detected amount of movement of the body portion of the user in a direction parallel to the display is a given detected amount;

(2) the determined amount of translatory movement of the camera is a second determined amount which is smaller than the first determined amount when the magnification of the image of the object within the field of view of the camera displayed on the display is a second magnification larger than the first magnification, the distance of the body portion of the user from the display is the first head distance, the distance of the camera from the field of view of the camera is the first camera distance, and the detected amount of movement of the body portion of the user in the direction parallel to the display is the given detected amount;

(3) the determined amount of translatory movement of the camera is a third determined amount which is smaller than the first determined amount when the magnification of the image of the object within the field of view of the camera displayed on the display is the first magnification, the distance of the body portion of the user from the display is a second body portion distance which is smaller than the first body portion distance, the distance of the camera from the field of view of the camera is the first camera distance, and the detected amount of movement of the body portion of the user in the direction parallel to the display is the given detected amount; and (4) the determined amount of translatory movement of the camera is a fourth determined amount which is smaller than the first determined amount when the magnification of the image of the object within the field of view of the camera displayed on the display is the first magnification, the distance of the body portion of the user from the display is the first body portion distance, the distance of the camera from the field of view of the camera is a second camera distance which is smaller than the first camera distance, and the detected amount of movement of the body portion of the user in the direction parallel to the display is the given detected amount.

According to another aspect of the disclosure, the moving of the camera by the determined amount of movement includes to maintain an orientation of the at least one camera constant while the camera is moved by the determined amount of translatory movement.

According to an aspect of the disclosure, the determined amount of movement of the camera includes an amount of rotatory movement of the camera. The amount of rotatory movement of the camera is determined in dependence of the detected amount of rotatory movement of the body portion of the user. The dependency between the determined amount of rotatory movement of the camera and the detected amount of rotatory movement of the body portion of the user depends on the magnification of the image of an object within the field of view of the camera displayed on the display, the distance of the body portion of the user from the display, the distance of the camera from the field of view of the camera, and the detected amount of the rotatory movement of the body portion of the user.

According to an aspect of the disclosure, the dependency between the determined amount of rotatory movement of the camera and the detected amount of rotatory movement of the body portion of the user is configured such that the determined amount of the rotatory movement of the camera decreases when the magnification of the image of the object within the field of view of the camera displayed on the display increases.

According to a further aspect of the disclosure, the dependency between the determined amount of rotatory movement of the camera and the detected amount of rotatory movement of the body portion of the user is configured such that the determined amount of the rotatory movement of the camera decreases when the distance of the body portion of the user from the display decreases.

According to a further aspect of the disclosure, the dependency between the determined amount of rotatory movement of the camera and the detected amount of rotatory movement of the body portion of the user is configured such that the determined amount of the rotatory movement of the camera decreases when the distance of the camera from the field of view of the camera decreases.

According to an aspect of the disclosure, the determining of the amount of movement of the camera is performed such that:

(1) the determined amount of rotatory movement of the camera is a first determined amount when a magnification of an image of an object within the field of view of the camera displayed on the display is a first magnification, a distance of the body portion of the user from the display is a first body portion distance, a distance of the camera from the field of view of the camera is a first camera distance, and the detected amount of rotatory movement of the body portion of the user is a given detected amount;

(2) the determined amount of rotatory movement of the camera is a second determined amount which is smaller than the first determined amount when the magnification of the image of the object within the field of view of the camera displayed on the display is a second magnification larger than the first magnification, the distance of the body portion of the user from the display is the first head distance, the distance of the camera from the field of view of the camera is the first camera distance, and the detected amount of rotatory movement of the body portion of the user is the given detected amount;

(3) the determined amount of rotatory movement of the camera is a third determined amount which is smaller than the first determined amount when the magnification of the image of the object within the field of view of the camera displayed on the display is the first magnification, the distance of the body portion of the user from the display is a second body portion distance which is smaller than the first body portion distance, the distance of the camera from the field of view of the camera is the first camera distance, and the detected amount of rotatory movement of the body portion of the user is the given detected amount; and (4) the determined amount of rotatory movement of the camera is a fourth determined amount which is smaller than the first determined amount when the magnification of the image of the object within the field of view of the camera displayed on the display is the first magnification, the distance of the body portion of the user from the display is the first body portion distance, the distance of the camera from the field of view of the camera is a second camera distance which is smaller than the first camera distance, and the detected amount of rotatory movement of the body portion of the user is the given detected amount.

According to an aspect of the disclosure, the determined amount of movement of the camera includes an amount of rotatory movement of the camera, wherein the determining of the amount of movement of the camera is further performed such that a portion of an object located within the field of view of the camera before the moving of the camera by the determined amount of movement is also located within the field of view of the camera when the moving of the camera by the determined amount of movement is completed. This may result in a change of the direction of view of the camera without changing of the location of the object located at the center of the field of view of the camera, for example.

According to an aspect of the disclosure, the method includes detecting of a start command, wherein the moving of the camera by the determined amount of movement is performed only after the start command has been detected.

Moreover, according to further aspect of the disclosure, the method further includes detecting of a stop command, wherein the moving of the camera is performed only until the stop command has been detected.

According to a further aspect of the disclosure, a method of operating the surgical microscope includes detecting an amount of a movement of a body portion of a user, determining an amount of change of the image magnification based on the detected movement of the body portion of the user; and changing the image magnification by the determined amount of change of the image magnification.

According to an aspect of the disclosure, the amount of change of the image magnification is determined in dependence of the detected amount of movement of the body portion of the user in a direction perpendicular to the display.

The dependency between the determined amount of change of the image magnification and the detected amount of movement of the body portion of the user in the direction perpendicular to the display depends on a magnification of an image of an object within the field of view of the camera displayed on the display, a distance of the body portion of the user from the display, a distance of the camera from the field of view of the camera, and the detected amount of movement of the body portion of the user in the direction perpendicular to the display.

According to an aspect of the disclosure, the dependency between the determined amount of change of the image magnification and the detected amount of movement of the body portion of the user in the direction perpendicular to the display is configured such that the determined amount of change of the image magnification decreases when the magnification of the image of the object within the field of view of the camera displayed on the display increases.

According to another aspect of the disclosure, the dependency between the determined amount of change of the image magnification and the detected amount of movement of the body portion of the user in the direction perpendicular to the display is configured such that the determined amount of change of the image magnification decreases when the distance of the body portion of the user from the display decreases.

According to an aspect of the disclosure, the dependency between the determined amount of change of the image magnification and the detected amount of movement of the body portion of the user in the direction perpendicular to the display is configured such that the determined amount of change of the image magnification decreases when the distance of the camera from the field of view of the camera decreases.

According to an aspect of the disclosure, the determining of the amount of change of the image magnification is performed such that:

(1) the determined amount of change of the image magnification is a first determined amount when
a magnification of an image of an object within the field of view of the camera displayed on the display is a first magnification,
a distance of the body portion of the user from the display is a first body portion distance,
a distance of the camera from the field of view of the camera is a first camera distance, and
the detected amount of movement of the body portion of the user in a direction perpendicular to the display is a given detected amount;

(2) the determined amount of change of the image magnification is a second determined amount which is smaller than the first determined amount when
the magnification of the image of the object within the field of view of the camera displayed on the display is a second magnification larger than the first magnification,
the distance of the body portion of the user from the display is the first body portion distance,
the distance of the camera from the field of view of the camera is the first camera distance, and
the detected amount of movement of the body portion of the user in the direction perpendicular to the display is the given detected amount;

(3) the determined amount of change of the image magnification is a third determined amount which is smaller than the first determined amount when
the magnification of the image of the object within the field of view of the camera displayed on the display is the first magnification,
the distance of the body portion of the user from the display is a second body portion distance which is smaller than the first body portion distance,
the distance of the camera from the field of view of the camera is the first camera distance, and
the detected amount of movement of the body portion of the user in the direction perpendicular to the display is the given detected amount; and (4) the determined amount of change of the image magnification is a fourth determined amount which is smaller than the first determined amount when
the magnification of the image of the object within the field of view of the camera displayed on the display is the first magnification,
the distance of the body portion of the user from the display is the first body portion distance,
the distance of the camera from the field of view of the camera is a second camera distance which is smaller than the first camera distance, and
the detected amount of movement of the body portion of the user in the direction perpendicular to the display is the given detected amount.

According to an aspect of the disclosure, the determined amount of change of the image magnification is an increase of the image magnification, and the movement of the body portion of the user in the direction perpendicular to the display includes a movement of the body portion of the user towards the display.

According to an aspect of the disclosure, the determined amount of change of the image magnification is a decrease of the image magnification, and the movement of the body portion of the user in the direction perpendicular to the display includes a movement of the body portion of the user away from the display.

According to another aspect of the disclosure, the amount of change of the image magnification is an increase of the image magnification, and the changing of the image magnification includes at least one of moving the camera towards the object and increasing a magnification of the zoom lens of the camera.

According to an aspect of the disclosure, the amount of change of the image magnification is a decrease of the image magnification, and the changing of the image magnification includes at least one of moving the camera away from the object and decreasing a magnification of the zoom lens of the camera.

According to another aspect of the disclosure, the method further includes detecting of a start command, and the changing of the image magnification by the determined amount of change of the image magnification is performed only after the start command has been detected.

According to an aspect of the disclosure, the method further includes detecting of a stop command, and the changing of the image magnification by the determined amount of change of the image magnification is performed only until the stop command has been detected.

According to an aspect of the disclosure, the start command includes at least one of a voice command issued by the user, an operation of a button performed by the user, and a gesture of the user.

According to an aspect of the disclosure, the stop command includes at least one of a voice command issued by the user, an operation of a button performed by the user, and a gesture of the user.

According to an aspect of the disclosure, the body portion of the user includes at least one of a head of the user, a chest of the user and a shoulder of the user.

According to an aspect of the disclosure, the camera is a stereo camera configured to record a pair of stereo images. For example, the at least one camera may comprise two cameras for this purpose.

According to an aspect of the disclosure, the display is configured to display stereoscopic images. According to another aspect of the disclosure, the display is a head-mounted display which can be carried by the user of the surgical microscope. According to yet another aspect of the disclosure, the display includes a screen displaying the images obtained by processing the pair of stereo images, and a pair of glasses wearable by a user and allowing the user to see the displayed images obtained by processing left images of the pairs of stereo images with the left eye and to see the displayed images obtained by processing the right images of the pairs of stereo images with the right eye.

According to another aspect of the disclosure, the surgical microscope includes a controller configured to perform the methods illustrated above.

BRIEF DESCRIPTION OF THE DRAWINGS

The disclosure will now be described with reference to the drawings wherein.

DESCRIPTION OF EXEMPLARY EMBODIMENTS

Figure 1:
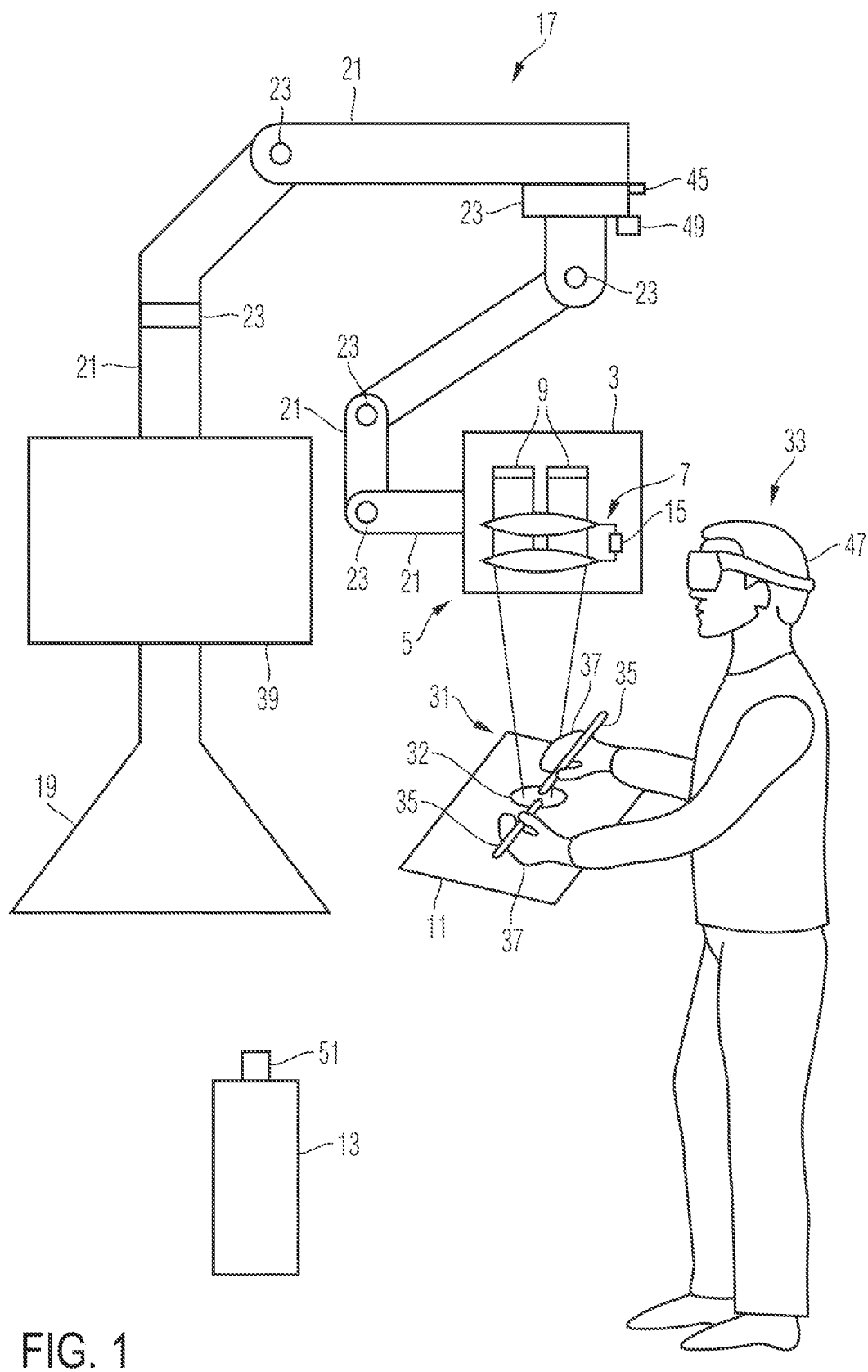
FIG. 1 shows a schematic illustration of a surgical microscope.

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

In the exemplary embodiments described below, components that are alike in function and structure are designated as far as possible by alike reference numerals. Therefore, to understand the features of the individual components of a specific exemplary embodiment, the descriptions of other exemplary embodiments and of the summary of the disclosure should be referred to.

FIG. 1 shows a schematic illustration of a surgical microscope 1. The surgical microscope 1 includes a microscope body 3, a housing, microscopy optics 5 including a magnifying zoom lens 7 and two cameras 9. The cameras 9 record images of a field of view of the cameras 9 in a focal plane 11. The optics 5 is configured to adjust a distance of the focal plane 11 from the microscope body by operating an actuator (not shown in FIG. 1) controlled by a controller 13 of the surgical microscope 1. Images of the field of view of the cameras 9 recorded by the cameras 9 are transmitted to the controller 13. The magnification of an object located in the field of view in the images recorded by the cameras 9 can be adjusted by the controller by operating an actuator 15 of the zoom lens 7.

The microscope body 3 is carried by a support 17 including a base 19 placed on a floor of an operation room, and plural members 21 connected by joints including actuators 23 controlled by the controller 13 in order to position the microscope body 3 within an accessible region of the operation room. The support 17 is configured to be controlled by the controller 13 such that the microscope body 3 performs both translatory movements in three independent directions and rotatory movements about three independent axes. Specifically, the actuators 23 of the support can be operated to position the cameras 9 such that the field of view of the cameras coincides with a surgical area 31 were a user 33 of the surgical microscope 1 performs a surgery with surgical tools 35 held by his hands 37. For this purpose, the user watches the surgical area 31 by looking at a display showing images transmitted from the controller 13. The images displayed on the display can be images obtained by processing the images recorded by the cameras 9. The processing of the images may include any image processing operation, such as cropping, rotating, contrast enhancement, color correction, and direct display of the recorded images without substantial changes to the image data.

The display can be, for example a flat panel display 39 which can be mounted on the support 17, or a head-mounted display 41 carried by the user 33.

The images recorded by the two cameras 9 are pairs of stereo images showing the surgical area from different angles. The pairs of stereo images can be watched by the user using the head-mounted display 41 so that the user 33 perceives a three-dimensional impression of the surgical area. Similarly, also the flat panel display 39 can be configured to display stereo images, wherein the user 33 will wear suitable glasses selecting the displayed images transmitted to the left and right eyes of the user. For example, the flat panel display 39 may alternatingly display the images for the left and right eyes while the glasses are active shutter glasses alternatingly transmitting light to the left and right eyes of the user 33. Moreover, the flat panel display 39 may display the images for the left and right eye of the user simultaneously using different polarization states of pixels of the screen, wherein the user 33 carries corresponding polarizing glasses.

The surgical microscope 1 further includes a sensor 45 allowing the controller to determine a position and orientation of a body portion, such as a head 47 of the user 33, relative to the microscope body 3, relative to the field of view 11 of the cameras 9 or relative to some other suitable position within the operation room. The sensor 45 can be mounted at any suitable position, such as an element of the support 17, on the display, 39 and 41. Moreover, the sensor may include plural sensor elements arranged at plural distributed locations.

The surgical microscope 1 further includes a sensor 49 allowing the controller 13 to determine a direction of gaze of the user 33. Specifically, the controller 13 may determine a position within the images displayed on the display 39 and 41 at which the eyes of the user are directed. Also, the sensor 49 can be mounted at any suitable position, such as an element of the support 17, on the display, 39 and 41. Moreover, the sensor may include plural sensor elements arranged at plural distributed locations.

The surgical microscope 1 further includes a sensor 51 allowing the controller 13 to receive commands issued by the user 33. For example, the sensor 51 may include a switch operated by the user 33 to enter a start command and a stop command. Moreover, the sensor 51 may include a microphone allowing the controller 13 to detect voice commands, such as "start" and "stop".

Figure 2:
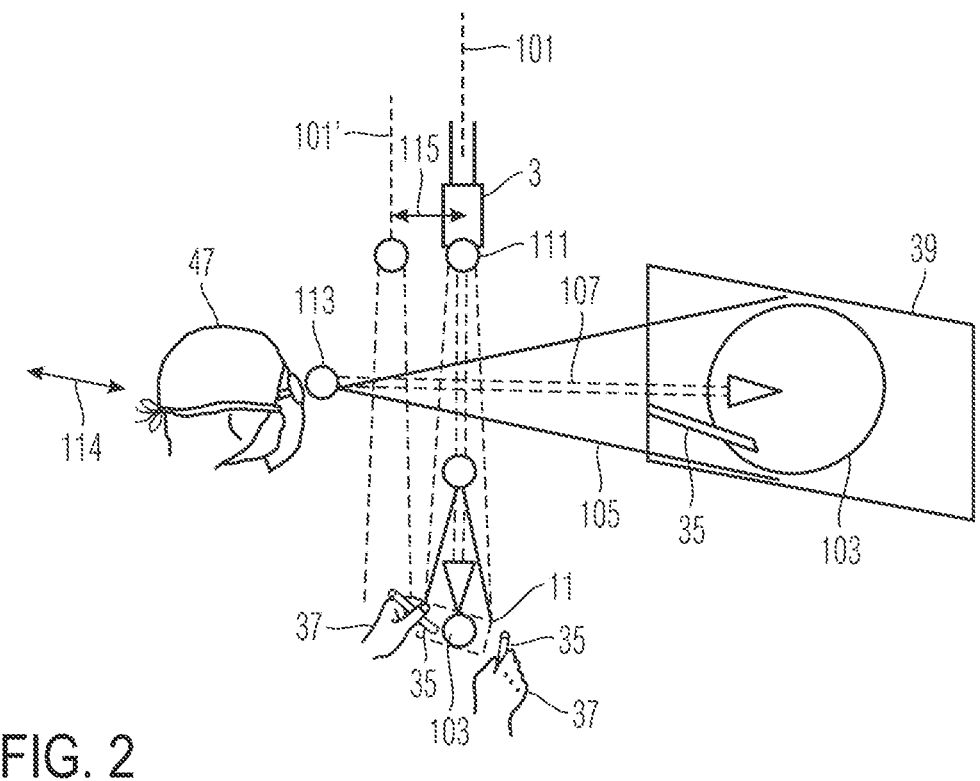
FIG. 2 shows a translatory movement of the cameras of the surgical microscope shown in FIG. 1.

FIG. 2 illustrates a translatory movement of the cameras included in the microscope body 3. Subsequent to a start command, the user performs a translatory movement of the head 47. The amount of translatory movement of the head of the user determines the amount of translatory movement of the cameras. A main axis 101 of the cameras 9 is arranged such that a circular object 103 is arranged at the center of the field of view 11 of the cameras 9. An image of the field of view 11 is recorded by the cameras 3 and displayed on the display 39. The display 39 is located within the users view as indicated by a cone 105, and the user gazes at the center of the image of the object 103 as indicated by an arrow 107.

A reference position of the microscope body 3 is indicated at 111. This reference position 111 can be used to determine a distance between the cameras 9 and the field of view 11 of the cameras 9.

A reference position of the head 47 of the user 33 is indicated at 113. The reference position 113 can be used to determine a distance between the head 47 or eyes of the user and the display 39.

The user 33 may initiate a process of positioning the cameras 3 relative to the object 103 by issuing a predefined start command recognized by the surgical microscope. Upon receipt of the start command, the surgical microscope tracks the position of the head 47 of the user and determines an amount of movement of the head of the user 47 until a stop command is detected. In the example shown in FIG. 2, the detected movement of the head 47 is a translatory movement parallel to the display 39 as indicated by an arrow 114 in FIG. 2. The surgical microscope determines an amount of movement of the camera based on the detected amount of movement of the head of the user, and the cameras 3 are moved by the determined amount of movement. In the exemplary embodiment shown in FIG. 2, the resulting movement of the camera is a translatory movement as indicated by an arrow 115 in FIG. 2.

Figure 3:
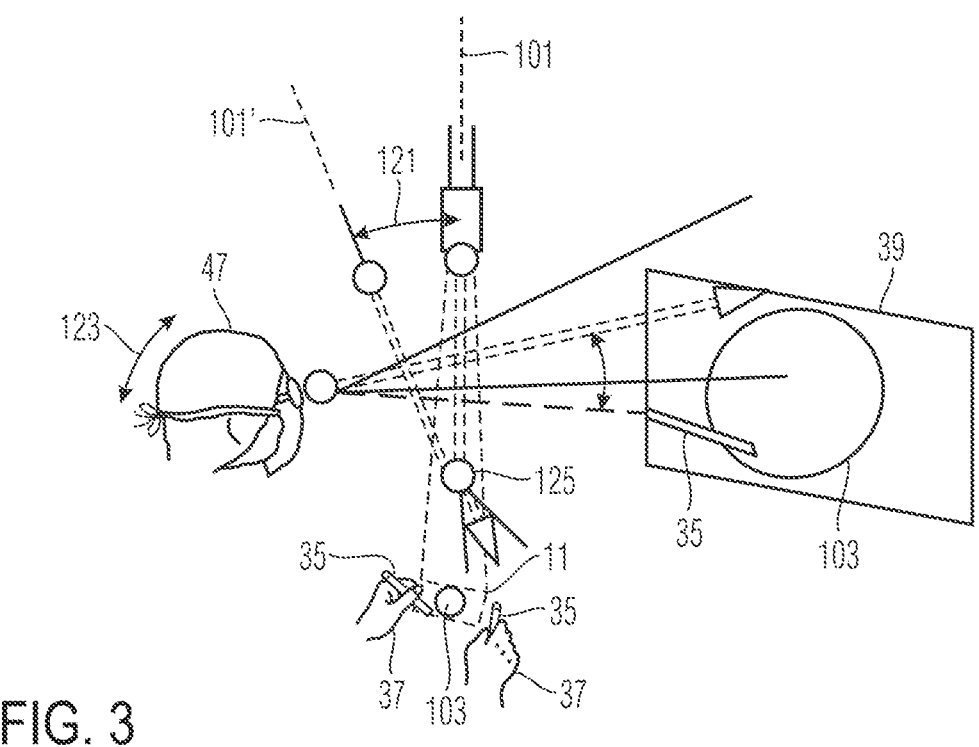
FIG. 3 shows a rotatory movement of the cameras of the surgical microscope of FIG. 1.

FIG. 3 illustrates a rotatory movement of the cameras included in the microscope body 3. Subsequent to a start command, the user performs a rotatory movement of the head 47. The amount of rotatory movement of the head of the user determines the amount of rotatory movement of the cameras.

In the exemplary embodiment shown in FIG. 3, the detected movement of the head 47 is a rotatory movement as indicated by an arrow 123 in FIG. 3. The surgical microscope determines an amount of rotary movement of the cameras based on the detected amount of movement of the head of the user, and the cameras 3 are rotated by the determined amount of movement. In addition, the cameras are translated by an amount such that the main axis 101 of the cameras is rotated about a center 125 located between the cameras 9 and the field of view 11 of the cameras 9. The combination of the translatory and rotatory movement result in a combined movement resembling a rotation of the cameras about the center 125.

Figure 4:
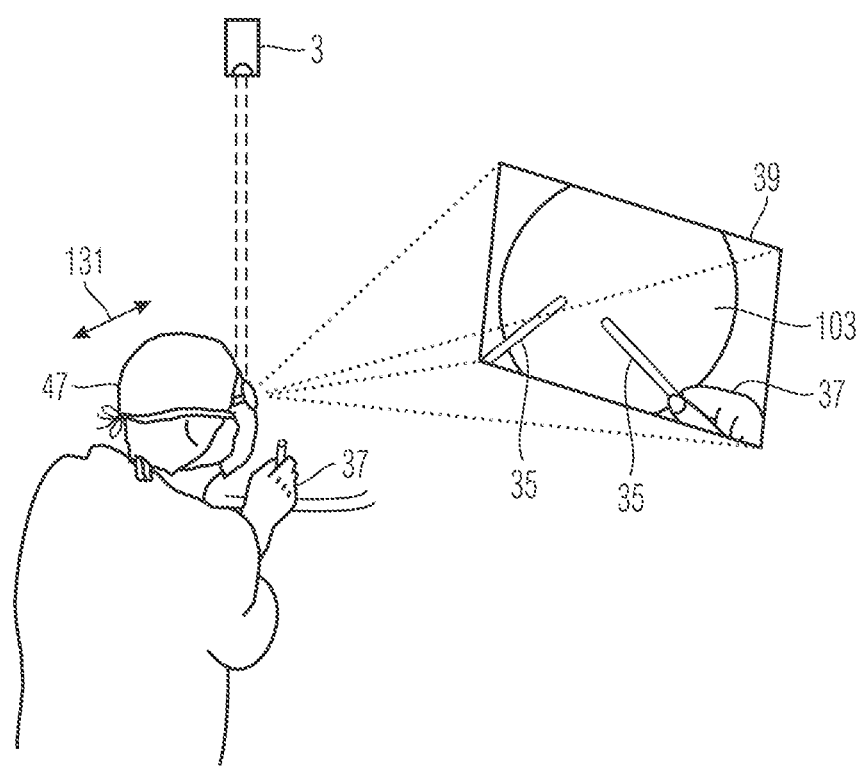
FIG. 4 shows a change of magnification of the surgical microscope of FIG. 1.

FIG. 4 illustrates a change of the image magnification provided by the surgical microscope. The image magnification can be defined as a ratio between a diameter of the image of the object 103 on the display 39 divided by a diameter of the object itself. The image magnification can be increased by moving the cameras closer to the object, by operating the zoom lens of the camera to zoom in, or by processing the image recorded by the cameras such that the processed image displayed on the display 39 and 41 in enlarged.

In the exemplary embodiment shown in FIG. 4, the detected movement of the head 47 is a translatory movement perpendicular to the display 39 as indicated by an arrow 131 in FIG. 4. The surgical microscope determines an amount of the change of the magnification of the microscope based on the detected amount of movement of the head of the user. In the exemplary embodiment shown FIG. 4, it is assumed that the user has moved his head towards the display 39, and that this movement results in an increase of the magnification provided by the surgical microscope. It is apparent from FIG. 4 that the object 103 displayed on the display 39 has a larger diameter than in FIGS. 2 and 3. Similarly, a movement of the head 47 away from the display 39 will result in a reduction of the magnification provided by the surgical microscope.

The amounts of changes of the microscopy optics illustrated with reference to FIGS. 2, 3, and 4 above, i.e., the translatory movement shown in FIG. 2, the rotary movement shown in FIG. 3, and the change of magnification shown in FIG. 4 depending on the amounts of the detected movements of the head of the user. Herein, the dependency between the detected movements of the head and the resulting change of the microscopy optics is not constant for all situations. Instead, this dependency depends on the magnification of the image of the object within the field of view of the camera displayed on the display, the distance of the body portion of the user from the display, and the distance of the camera from the field of view of the camera.

Specifically, these amounts of changes decrease with increasing magnification provided by the surgical microscope, they decrease with decreasing distances of the body portion of the user from the display, and they decrease with decreasing distance of the cameras from the field of view of the cameras.

In the exemplary embodiments illustrated above, the user can control the location and orientation of the camera and the magnification provided by the surgical microscope by performing movements of the head or some other body portion. Herein, it is possible to define common start and stop commands for all three operations, or to define separate start and/or stop commands of the individual operations.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

What is claimed is:

1. A method of operating a surgical microscope, the surgical microscope including at least one camera having a field of view, a support for the at least one camera, the support including at least one actuator for positioning the at least one camera relative to an object, and a display configured to display images recorded by the at least one camera, the method comprising:

detecting an amount of movement of a body portion of a user;

determining an amount of movement of the at least one camera based on the detected amount of movement of the body portion of the user; and moving the at least one camera by the determined amount of movement of the at least one camera, wherein the determined amount of movement of the at least one camera includes an amount of translatory movement in a direction transverse to a line connecting the at least one camera and the field of view, and wherein the determining of the amount of movement of the at least one camera is performed such that:

(1) the amount of translatory movement of the at least one camera is a first determined amount when a magnification of an image of the object within the field of view of the at least one camera displayed on the display is a first magnification, a distance of the body portion of the user from the display is a first body portion distance, a distance of the at least one camera from the field of view of the at least one camera is a first camera distance, and a detected amount of movement of the body portion of the user in a direction parallel to the display is a given detected amount, (2) the amount of translatory movement of the at least one camera is a second determined amount which is smaller than the first determined amount when the magnification of the image of the object within the field of view of the at least one camera displayed on the display is a second magnification larger than the first magnification, the distance of the body portion of the user from the display is the first body portion distance, the distance of the at least one camera from the field of view of the at least one camera is the first camera distance, and the detected amount of movement of the body portion of the user in the direction parallel to the display is the given detected amount, (3) the amount of translatory movement of the at least one camera is a third determined amount which is smaller than the first determined amount when the magnification of the image of the object within the field of view of the at least one camera displayed on the display is the first magnification, the distance of the body portion of the user from the display is a second body portion distance which is smaller than the first body portion distance, the distance of the at least one camera from the field of view of the at least one camera is the first camera distance, and the detected amount of movement of the body portion of the user in the direction parallel to the display is the given detected amount, and (4) the amount of translatory movement of the at least one camera is a fourth determined amount which is smaller than the first determined amount when the magnification of the image of the object within the field of view of the at least one camera displayed on the display is the first magnification, the distance of the body portion of the user from the display is the first body portion distance, the distance of the at least one camera from the field of view of the at least one camera is a second camera distance which is smaller than the first camera distance, and the detected amount of movement of the body portion of the user in the direction parallel to the display is the given detected amount.

2. The method of claim 1, wherein the moving of the at least one camera by the determined amount of movement includes to maintain an orientation of the at least one camera constant while moving of the at least one camera by the amount of translatory movement.

3. The method of claim 1, wherein the determined amount of movement of the at least one camera includes an amount of rotatory movement of the at least one camera, and wherein the determining of the amount of movement of the at least one camera is further performed such that a portion of the object located within the field of view of the at least one camera before the moving of the at least one camera by the determined amount of movement is also located within the field of view of the at least one camera when the moving of the at least one camera by the determined amount of movement is completed.

4. The method of claim 1, further comprising detecting a start command, wherein the moving of the at least one camera by the determined amount of movement of the at least one camera is performed only after the start command has been detected.

5. The method of claim 4, wherein the start command includes at least one of a voice command issued by the user, an operation of a button performed by the user, and a gesture of the user.

6. The method of claim 1, further comprising detecting a stop command, wherein the moving of the at least one camera is performed only until the stop command has been detected.

7. The method of claim 6, wherein the stop command includes at least one of a voice command issued by the user, an operation of a button performed by the user, and a gesture of the user.

8. The method of claim 1, wherein the detecting of the amount of movement of the body portion of the user includes at least one of detecting an amount of movement of a head of the user, detecting an amount of movement of a chest of the user, and detecting an amount of movement of a shoulder of the user.

9. The method of claim 1, wherein the at least one camera is a stereo camera.

10. The method of claim 1, wherein the at least one camera includes two cameras.

11. The method of claim 1, wherein the display is configured to display stereoscopic images.

12. The method of claim 11, wherein the display is a head-mounted display.

13. The method of claim 11, wherein the display comprises a pair of glasses wearable by a user and alternatingly transmitting light to the left and right eyes of the user.

14. A method of operating a surgical microscope, the surgical microscope including at least one camera having a field of view, a support for the at least one camera, the support including at least one actuator for positioning the at least one camera relative to an object, and a display configured to display images recorded by the at least one camera, the method comprising:
  detecting an amount of movement of a body portion of a user;
  determining an amount of movement of the at least one camera based on the detected amount of movement of the body portion of the user; and
  moving the at least one camera by the determined amount of movement of the at least one camera,
  wherein the determined amount of movement of the at least one camera includes an amount of rotatory movement of the at least one camera, and
  wherein the determining of the amount of movement of the at least one camera is performed such that:
  (1) the amount of the rotatory movement of the at least one camera is a first determined amount when a magnification of an image of the object within the field of view of the at least one camera displayed on the display is a first magnification, a distance of the body portion of the user from the display is a first body portion distance, a distance of the at least one camera from the field of view of the at least one camera is a first camera distance, and an amount of rotatory movement of the body portion of the user is a given detected amount,
  (2) the amount of rotatory movement of the at least one camera is a second determined amount which is smaller than the first determined amount when the magnification of the image of the object within the field of view of the at least one camera displayed on the display is a second magnification larger than the first magnification, the distance of the body portion of the user from the display is the first body portion distance, the distance of the at least one camera from the field of view of the at least one camera is the first camera distance, and the amount of the rotatory movement of the body portion of the user is the given detected amount,
  (3) the amount of rotatory movement of the at least one camera is a third determined amount which is smaller than the first determined amount when the magnification of the image of the object within the field of view of the at least one camera displayed on the display is the first magnification, the distance of the body portion of the user from the display is a second body portion distance which is smaller than the first body portion distance, the distance of the at least one camera from the field of view of the at least one camera is the first camera distance, and the amount of the rotatory movement of the body portion of the user is the given detected amount, and
  (4) the amount of the rotatory movement of the at least one camera is a fourth determined amount which is smaller than the first determined amount when the magnification of the image of the object within the field of view of the at least one camera displayed on the display is the first magnification, the distance of the body portion of the user from the display is the first body portion distance, the distance of the at least one camera from the field of view of the at least one camera is a second camera distance which is smaller than the first camera distance, and the amount of the rotatory movement of the body portion of the user is the given detected amount.

15. The method of claim 14, wherein the determining of the amount of movement of the at least one camera is further performed such that a portion of the object located within the field of view of the at least one camera before the moving of the at least one camera by the determined amount of movement is also located within the field of view of the at least one camera when the moving of the at least one camera by the determined amount of movement is completed.

16. The method of claim 14, further comprising detecting a start command,
  wherein the moving of the at least one camera by the determined amount of movement of the at least one camera is performed only after the start command has been detected.

17. The method of claim 16, wherein the start command includes at least one of a voice command issued by the user, an operation of a button performed by the user, and a gesture of the user.

18. The method of claim 14, further comprising detecting a stop command,
  wherein the moving of the at least one camera is performed only until the stop command has been detected.

19. The method of claim 18, wherein the stop command includes at least one of a voice command issued by the user, an operation of a button performed by the user, and a gesture of the user.

20. The method of claim 14, wherein the detecting of the amount of movement of the body portion of the user includes at least one of detecting an amount of movement of a head of the user, detecting an amount of movement of a chest of the user, and detecting an amount of movement of a shoulder of the user.

21. The method of claim 14, wherein the at least one camera is a stereo camera.

22. The method of claim 14, wherein the at least one camera includes two cameras.

23. The method of claim 14, wherein the display is configured to display stereoscopic images.

24. The method of claim 23, wherein the display is a head-mounted display.

25. The method of claim 24, wherein the display comprises a pair of glasses wearable by a user and alternatingly transmitting light to the left and right eyes of the user.

26. A method of operating a surgical microscope, the surgical microscope including at least one camera having a zoom lens, a support for the at least one camera, the support including at least one actuator for positioning the at least one camera relative to an object, and a display configured to display images of the object recorded by the at least one camera using an image magnification, the method comprising:
  detecting an amount of movement of a body portion of a user;
  determining an amount of change of the image magnification based on the detected amount of movement of the body portion of the user; and
  changing the image magnification by the determined amount of change of the image magnification, wherein the determining of the amount of the change of the image magnification is performed such that:
(1) the amount of change of the image magnification is a first determined amount when a magnification of an image of the object within a field of view of the at least one camera displayed on the display is a first magnification, a distance of the body portion of the user from the display is a first body portion distance, a distance of the at least one camera from the field of view of the at least one camera is a first camera distance, and the detected amount of movement of the body portion of the user in a direction perpendicular to the display is a given detected amount,
(2) the amount of change of the image magnification is a second determined amount which is smaller than the first determined amount when the magnification of the image of the object within the field of view of the at least one camera displayed on the display is a second magnification larger than the first magnification, the distance of the body portion of the user from the display is the first body portion distance, the distance of the at least one camera from the field of view of the at least one camera is the first camera distance, and the detected amount of movement of the body portion of the user in the direction perpendicular to the display is the given detected amount,
(3) the amount of change of the image magnification is a third determined amount which is smaller than the first determined amount when the magnification of the image of the object within the field of view of the at least one camera displayed on the display is the first magnification, the distance of the body portion of the user from the display is a second body portion distance which is smaller than the first body portion distance, the distance of the at least one camera from the field of view of the at least one camera is the first camera distance, and the detected amount of movement of the body portion of the user in the direction perpendicular to the display is the given detected amount, and
(4) the amount of change of the image magnification is a fourth determined amount which is smaller than the first determined amount when the magnification of the image of the object within the field of view of the at least one camera displayed on the display is the first magnification, the distance of the body portion of the user from the display is the first body portion distance, the distance of the at least one camera from the field of view of the at least one camera is a second camera distance which is smaller than the first camera distance, and the detected amount of movement of the body portion of the user in the direction perpendicular to the display is the given detected amount.

27. The method of claim 26, wherein the amount of change of the image magnification is an increase of the image magnification, and
wherein the detected amount of movement of the body portion of the user in the direction perpendicular to the display includes a detected amount of movement of the body portion of the user towards the display.

28. The method of claim 26, wherein the amount of change of the image magnification is a decrease of the image magnification, and
wherein the detected amount of movement of the body portion of the user in the direction perpendicular to the display includes a detected amount of movement of the body portion of the user away from the display.

29. The method of claim 26, wherein the amount of change of the image magnification is an increase of the image magnification, and
wherein the changing of the image magnification includes at least one of moving the at least one camera towards the object and increasing the magnification of the zoom lens of the at least one camera.

30. The method of claim 26, wherein the amount of change of the image magnification is a decrease of the image magnification, and
wherein the changing of the image magnification includes at least one of moving the at least one camera away from the object and decreasing the magnification of the zoom lens of the at least one camera.

31. The method of claim 26, further comprising detecting a start command,
wherein the changing of the image magnification by the determined amount of change of the image magnification is performed only after the start command has been detected.

32. The method of claim 31, wherein the start command includes at least one of a voice command issued by the user, an operation of a button performed by the user, and a gesture of the user.

33. The method of claim 26, further comprising detecting a stop command,
wherein the changing of the image magnification by the determined amount of change of the image magnification is performed only until the stop command has been detected.

34. The method of claim 33, wherein the stop command includes at least one of a voice command issued by the user, an operation of a button performed by the user, and a gesture of the user.

35. The method of claim 26, wherein the detecting of the amount of movement of the body portion of the user includes at least one of detecting an amount of movement of a head of the user, detecting an amount of movement of a chest of the user, and detecting an amount of movement of a shoulder of the user.

36. The method of claim 26, wherein the at least one camera is a stereo camera.

37. The method of claim 26, wherein the at least one camera includes two cameras.

38. The method of claim 26, wherein the display is configured to display stereoscopic images.

39. The method of claim 38, wherein the display is a head-mounted display.

40. The method of claim 38, wherein the display comprises a pair of glasses wearable by a user and alternatingly transmitting light to the left and right eyes of the user.

41. A surgical microscope comprising:
at least one camera having a field of view;
a support for the at least one camera, the support including at least one actuator, configured to position the at least one camera relative to an object;
a display configured to display images recorded by the at least one camera; and
a controller configured to control the surgical microscope in order to:
detect an amount of movement of a body portion of a user;
determine an amount of movement of the at least one camera based on the detected amount of movement of the body portion of the user; and
move the at least one camera by the determined amount of movement of the at least one camera, wherein the determined amount of movement of the at least one camera includes an amount of translatory movement in a direction transverse to a line connecting the at least one camera and the field of view, and wherein the determining of the amount of movement of the at least one camera is performed such that:

(1) the amount of translatory movement of the at least one camera is a first determined amount when a magnification of an image of the object within the field of view of the at least one camera displayed on the display is a first magnification, a distance of the body portion of the user from the display is a first body portion distance, a distance of the at least one camera from the field of view of the at least one camera is a first camera distance, and a detected amount of movement of the body portion of the user in a direction parallel to the display is a given detected amount, (2) the amount of translatory movement of the at least one camera is a second determined amount which is smaller than the first determined amount when the magnification of the image of the object within the field of view of the at least one camera displayed on the display is a second magnification larger than the first magnification, the distance of the body portion of the user from the display is the first body portion distance, the distance of the at least one camera from the field of view of the at least one camera is the first camera distance, and the detected amount of movement of the body portion of the user in the direction parallel to the display is the given detected amount, (3) the amount of translatory movement of the at least one camera is a third determined amount which is smaller than the first determined amount when the magnification of the image of the object within the field of view of the at least one camera displayed on the display is the first magnification, the distance of the body portion of the user from the display is a second body portion distance which is smaller than the first body portion distance, the distance of the at least one camera from the field of view of the at least one camera is the first camera distance, and the detected amount of movement of the body portion of the user in the direction parallel to the display is the given detected amount, and (4) the amount of translatory movement of the at least one camera is a fourth determined amount which is smaller than the first determined amount when the magnification of the image of the object within the field of view of the at least one camera displayed on the display is the first magnification, the distance of the body portion of the user from the display is the first body portion distance, the distance of the at least one camera from the field of view of the at least one camera is a second camera distance which is smaller than the first camera distance, and the detected amount of movement of the body portion of the user in the direction parallel to the display is the given detected amount.

42. The surgical microscope of claim 41, wherein the controller is configured to maintain an orientation of the at least one camera constant while moving of the at least one camera by the amount of translatory movement.

43. The surgical microscope of claim 41, wherein the determined amount of movement of the at least one camera includes an amount of rotatory movement of the at least one camera, and wherein the controller is configured to determine the amount of the movement of the at least one camera such that a portion of the object located within the field of view of the at least one camera before the moving of the at least one camera by the determined amount of movement is also located within the field of view of the at least one camera when the moving of the at least one camera by the determined amount of movement is completed.

44. The surgical microscope of claim 41, wherein the controller is configured to detect a start command, and to move the at least one camera by the determined amount of movement of the at least one camera only after the start command has been detected; and wherein the start command includes at least one of a voice command issued by the user, an operation of a button performed by the user, and a gesture of the user.

45. The surgical microscope of claim 41, wherein the controller is configured to detect a stop command, and to move of the at least one camera only until the stop command has been detected, and wherein the stop command includes at least one of a voice command issued by the user, an operation of a button performed by the user, and a gesture of the user.

46. The surgical microscope of claim 41, wherein the controller is further configured to detect at least one of an amount of movement of a head of the user, an amount of movement of a chest of the user, and an amount of movement of a shoulder of the user.

47. The surgical microscope of claim 41, wherein the at least one camera is a stereo camera.

48. The surgical microscope of claim 41, wherein the at least one camera includes two cameras.

49. The surgical microscope of claim 41, wherein the display is configured to display stereoscopic images.

50. The surgical microscope of claim 49, wherein the display is a head-mounted display.

51. The surgical microscope of claim 49, wherein the display comprises a pair of glasses wearable by a user and alternatingly transmitting light to the left and right eyes of the user.

52. A surgical microscope comprising:

at least one camera having a field of view;

a support for the at least one camera, the support including at least one actuator, configured to position the at least one camera relative to an object;

a display configured to display images recorded by the at least one camera; and a controller configured to control the surgical microscope in order to:

detect an amount of movement of a body portion of a user;

determine an amount of movement of the at least one camera based on the detected amount of movement of the body portion of the user; and move the at least one camera by the determined amount of movement of the at least one camera, wherein the determined amount of movement of the at least one camera includes an amount of rotatory movement of the at least one camera, and wherein the determining of the amount of movement of the at least one camera is performed such that:

(1) the amount of the rotatory movement of the at least one camera is a first determined amount when a magnification of an image of the object within the field of view of the at least one camera displayed on the display is a first magnification, a distance of the body portion of the user from the display is a first body portion distance, a distance of the at least one camera from the field of view of the at least one camera is a first camera distance, and an amount of rotatory movement of the body portion of the user is a given detected amount, (2) the amount of rotatory movement of the at least one camera is a second determined amount which is smaller than the first determined amount when the magnification of the image of the object within the field of view of the at least one camera displayed on the display is a second magnification larger than the first magnification, the distance of the body portion of the user from the display is the first body portion distance, the distance of the at least one camera from the field of view of the at least one camera is the first camera distance, and the amount of the rotatory movement of the body portion of the user is the given detected amount, (3) the amount of rotatory movement of the at least one camera is a third determined amount which is smaller than the first determined amount when the magnification of the image of the object within the field of view of the at least one camera displayed on the display is the first magnification, the distance of the body portion of the user from the display is a second body portion distance which is smaller than the first body portion distance, the distance of the at least one camera from the field of view of the at least one camera is the first camera distance, and the amount of the rotatory movement of the body portion of the user is the given detected amount, and (4) the amount of the rotatory movement of the at least one camera is a fourth determined amount which is smaller than the first determined amount when the magnification of the image of the object within the field of view of the at least one camera displayed on the display is the first magnification, the distance of the body portion of the user from the display is the first body portion distance, the distance of the at least one camera from the field of view of the at least one camera is a second camera distance which is smaller than the first camera distance, and the amount of the rotatory movement of the body portion of the user is the given detected amount.

53. The surgical microscope of claim 52, wherein the controller is configured to determine the amount of movement of the at least one camera such that a portion of the object located within the field of view of the at least one camera before the moving of the at least one camera by the determined amount of movement is also located within the field of view of the at least one camera when the moving of the at least one camera by the determined amount of movement is completed.

54. The surgical microscope of claim 52, wherein the controller is further configured to detect a start command and to move the at least one camera by the determined amount of movement of the at least one camera only after the start command has been detected, and
wherein the start command includes at least one of a voice command issued by the user, an operation of a button performed by the user, and a gesture of the user.

55. The surgical microscope of claim 52, wherein the controller is further configured to detect a stop command and to move of the at least one camera by the determined amount of movement of the at least one camera only until the stop command has been detected, and
wherein the stop command includes at least one of a voice command issued by the user, an operation of a button performed by the user, and a gesture of the user.

56. The surgical microscope of claim 52, wherein the controller is further configured to detect at least one of an amount of movement of a head of the user, an amount of movement of a chest of the user, and an amount of movement of a shoulder of the user.

57. The surgical microscope of claim 52, wherein the at least one camera is a stereo camera.

58. The surgical microscope of claim 52, wherein the at least one camera includes two cameras.

59. The surgical microscope of claim 52, wherein the display is configured to display stereoscopic images.

60. The surgical microscope of claim 59, wherein the display is a head-mounted display.

61. The surgical microscope of claim 59, wherein the display comprises a pair of glasses wearable by a user and alternatingly transmitting light to the left and right eyes of the user.

62. A surgical microscope comprising:
at least one camera having a field of view;
a support for the at least one camera, the support including at least one actuator, configured to position the at least one camera relative to an object;
a display configured to display images recorded by the at least one camera using an image magnification; and
a controller configured to control the surgical microscope in order to:
detect an amount of movement of a body portion of a user;
determine an amount of change of the image magnification based on the detected amount of movement of the body portion of the user; and
change the image magnification by the determined amount of change of the image magnification, wherein the determining of the amount of the change of the image magnification is performed such that:

(1) the amount of change of the image magnification is a first determined amount when a magnification of an image of the object within a field of view of the at least one camera displayed on the display is a first magnification, a distance of the body portion of the user from the display is a first body portion distance, a distance of the at least one camera from the field of view of the at least one camera is a first camera distance, and the detected amount of movement of the body portion of the user in a direction perpendicular to the display is a given detected amount, (2) the amount of change of the image magnification is a second determined amount which is smaller than the first determined amount when the magnification of the image of the object within the field of view of the at least one camera displayed on the display is a second magnification larger than the first magnification, the distance of the body portion of the user from the display is the first body portion distance, the distance of the at least one camera from the field of view of the at least one camera is the first camera distance, and the detected amount of movement of the body portion of the user in the direction perpendicular to the display is the given detected amount, (3) the amount of change of the image magnification is a third determined amount which is smaller than the first determined amount when the magnification of the image of the object within the field of view of the at least one camera displayed on the display is the first magnification, the distance of the body portion of the user from the display is a second body portion distance which is smaller than the first body portion distance, the distance of the at least one camera from the field of view of the at least one camera is the first camera distance, and the detected amount of movement of the body portion of the user in the direction perpendicular to the display is the given detected amount, and (4) the amount of change of the image magnification is a fourth determined amount which is smaller than the first determined amount when the magnification of the image of the object within the field of view of the at least one camera displayed on the display is the first magnification, the distance of the body portion of the user from the display is the first body portion distance, the distance of the at least one camera from the field of view of the at least one camera is a second camera distance which is smaller than the first camera distance, and the detected amount of movement of the body portion of the user in the direction perpendicular to the display is the given detected amount.

63. The surgical microscope of claim 62, wherein the amount of change of the image magnification is an increase of the image magnification, and wherein the detected amount of movement of the body portion of the user in the direction perpendicular to the display includes a detected amount of movement of the body portion of the user towards the display.

64. The surgical microscope of claim 62, wherein the amount of change of the image magnification is a decrease of the image magnification, and wherein the detected amount of movement of the body portion of the user in the direction perpendicular to the display includes a detected amount of movement of the body portion of the user away from the display.

65. The surgical microscope of claim 62, wherein the amount of change of the image magnification is an increase of the image magnification, and wherein the changing of the image magnification includes at least one of moving the at least one camera towards the object and increasing the magnification of the zoom lens of the at least one camera.

66. The surgical microscope of claim 62, wherein the amount of change of the image magnification is a decrease of the image magnification, and wherein the changing of the image magnification includes at least one of moving the at least one camera away from the object and decreasing the magnification of the zoom lens of the at least one camera.

67. The surgical microscope of claim 62, wherein the controller is configured to detect a start command, and to change the image magnification by the determined amount of change of the image magnification only after the start command has been detected, and wherein the start command includes at least one of a voice command issued by the user, an operation of a button performed by the user, and a gesture of the user.

68. The surgical microscope of claim 62, wherein the controller is configured to detect a stop command, and to change the image magnification by the determined amount of change of the image magnification only until the stop command has been detected, and wherein the stop command includes at least one of a voice command issued by the user, an operation of a button performed by the user, and a gesture of the user.

69. The surgical microscope of claim 62, wherein the controller is configured to detect at least one of an amount of movement of a head of the user, an amount of movement of a chest of the user, and an amount of movement of a shoulder of the user.

70. The surgical microscope of claim 62, wherein the at least one camera is a stereo camera.

71. The surgical microscope of claim 62, wherein the at least one camera includes two cameras.

72. The surgical microscope of claim 62, wherein the display is configured to display stereoscopic images.

73. The surgical microscope of claim 72, wherein the display is a head-mounted display.

74. The surgical microscope of claim 72, wherein the display comprises a pair of glasses wearable by a user and alternatingly transmitting light to the left and right eyes of the user.

* * * * *